United States Patent [19]
Largman et al.

[11] Patent Number: 5,837,507
[45] Date of Patent: Nov. 17, 1998

[54] HOX-INDUCED ENHANCEMENT OF IN VIVO AND IN VITRO PROLIFERATIVE CAPACITY AND GENE THERAPEUTIC METHODS

[75] Inventors: Corey Largman, Berkley; Hugh Jeffrey Lawrence, Lafayette, both of Calif.; R. Keith Humphries, Vancouver, Canada; Guy Sauvageau, 7390 De Tilly, Montreal, P.O., Canada, H3R 3E3

[73] Assignees: The Regents of the University of California; Keith Humphries; Guy Sauvageau, all of Oakland, Calif.

[21] Appl. No.: 557,973

[22] Filed: Nov. 13, 1995

[51] Int. Cl.$^6$ .............................. C12N 15/00; C12N 5/10
[52] U.S. Cl. .................................... 435/172.1; 435/172.3; 435/325; 435/372
[58] Field of Search ................................ 424/93.7, 93.71, 424/93.72, 93.73; 435/172.1, 172.3, 240.1, 240.2, 325, 240, 372

[56] References Cited

U.S. PATENT DOCUMENTS 4,714,680  12/1987  Civin ................................ 435/240.25
5,460,964  10/1995  McGlave et al. .................. 435/240.21

OTHER PUBLICATIONS

Burglin, TR. in "Guidebook to Homebox Genes". Sambrook and Tooze. Duoule, D. editor. Oxford University Press, Oxford, UK. pp. 27–71, 1994.

Bachiller, Daniel, et al., Conservation of a functional hierarchy between mammalian and insect Hox/Hom genes, *EMBO J.*, 13:1930–1941, (1994).

Caré, A., et al., Coordinate Expression and Proliferative Role of HOXB Genes in Activated Adult T Lymphocytes, *Mol. Cell. Biol.*, 14:4872–4877, (1994).

Celetti, Angela, et al., Characteristics Patterns of Hox Gene Expression in Different Types of Human Leukemia, *Int. J. Cancer*, 53:237–244, (1993).

Civin, Curt, et al., Antigenic Analysis of Hematopoiesis, *J. Immunol.*, 133:157–165, (Jul. 1984).

Faiella, Antonio, et al., Inhibition of retinoic acid–induced activation if 3' human HOXB genes by antisense oligonucletides affects sequential activation of genes located upstream in the four HOX clusters, *Proc. Natl. Acad. Sci.*, 91:5335–5339.

Giampaolo, A. et al., Key Functional role and Lineage–Specific Expression of Selected HOXB Genes in Purified Hematopoietic Differentiation, *Blood*, 84:3637–3647, (Dec. 1, 1994).

Hawley, Robert, et al., The HOX11 homebox–containing gene of human leukemia immortalizers murine hematopoietic precursors, *Oncogene*, 9:1–12, (1992).

Lawrence, H. Jeffrey, et al., Homeobox Genes in Normal Hematopoiesis and Leukemia, *Blood*, vol. 80, No. 1, 2445–2453, (1992).

Lawrence, H. Jeffrey, et al., Sage– and lineage–specific expression of the HOXA10 homeobox gene in normal and leukemichematopoietic cells, *Exp. Hematol.*, 23:1160–1166, (1995).

Michael, Levine, et al., Homeobox Proteins as Sequence–Specific Transcription Factors, *Cell*, 55:537–540, (1988).

Lowney, P., et all., A human Hox 1 homeobox gene exhibits myeloid–specific expression of alternative transcripts in human hematopoietic cells, *Nucleic Acids Research*, vol. 19, No. 12, 3443–3449, (1991).

Magli, Maria Cristina, Coordinate regulation of Hox genes in human hematopoietc cells, *Proc. Natl. Acad. Sci.*, 88:6348–6352, (Jul. 1991).

Matthews, C.H.E., et al., Erythroid–Restricted Expression of Homeobox Genes of the Human HOX 2 Locus, *Blood* 78:2248–2252, (1991).

Perkins, Andrew, C., et. al., Conditional immortalization of mouse myelomonocytic, megakaryocytic and mast cell progenitors by the Hox–2.4 homeobox gene, *EMBO J.*, 12:3835–3846, (1993).

Piverali, Fiorenzo, A., et al., Expression of HOX homeogenes in human neuroblastoma cell culture lines, *Differentiation*, 45:61–69, (1990).

Sauvageau, Guy, et al., Differential expression of homeobox genes in functionally distinct CD34$^+$subpopulations of human bone marrow cells, *Proc. Natl. Acad. Sci.*, 91:12223–12227, (1984).

*Primary Examiner*—David Saunders
*Assistant Examiner*—F. Pierre VanderVegt
*Attorney, Agent, or Firm*—Karl Bozicevic; Bozicevic & Reed LLP

[57] ABSTRACT

Stem cells transduced with HOXB4 exhibit enhanced in vitro and in vivo ability for self-regeneration and generate higher-numbers of tranplantable pluripotent hematopoietic stem cells relative to control and nonmanipulated cells.

18 Claims, 4 Drawing Sheets

HOX-INDUCED ENHANCEMENT OF IN VIVO AND IN VITRO PROLIFERATIVE CAPACITY AND GENE THERAPEUTIC METHODS

STATEMENT AS TO FEDERALLY SPONSORED RESEARCH

The United States Government may have certain rights in this application pursuant to Grant No. HL48374 awarded by the National Institutes of Health.

FIELD OF THE INVENTION

This invention relates to methods of expanding stem cell populations, specifically, the use of HOX-induced expansion of primitive stem cells populations and therapeutic methods for using same.

BACKGROUND OF THE INVENTION

Hematopoietic stem cells (HSCs) are rare cells that have been identified in fetal bone marrow, umbilical cord blood, adult bone marrow, and peripheral blood, which are capable of differentiating into each of the myeloerythroid (red blood cells, granulocytes, monocytes), megakaryocyte (platelets) and lymphoid (T-cells, B-cells, and natural killer cells) lineages. In addition, these cells are long-lived, and are capable of producing additional stem cells, a process termed self-renewal. Stem cells initially undergo commitment to lineage restricted progenitor cells, which can be assayed by their ability to form colonies in semisolid media. Progenitor cells are restricted in their ability to undergo multi-lineage differentiation and have lost their ability to self-renew. Progenitor cells eventually differentiate and mature into each of the functional elements of the blood.

The lifelong maintenance of mature blood cells results from the proliferative activity of a small number of totipotent HSCs that have a high, but perhaps limited, capacity for self-renewal. Recently, much progress has been made in identifying a variety of cytokines that can regulate the cycling status of primitive hematopoietic cells (Ogawa (1993) Blood 81:2844–2853). However, the genetic mechanisms responsible for the intrinsic control of self-renewal and differentiation outcomes of HSC divisions remain largely undefined.

It is becoming increasingly apparent that distinct sub-populations of stem cells may be responsible for different phases of engraftment post transplantation. As early as 1964, differences in the ability of murine spleen colony forming units (CFU-S) to generate secondary CFU-S were defined (Ploemacher & Brons (1994) Exp. Hematol. 17:263–266). Although evidence now indicates that most CFU-S are not involved in repopulating lethally irradiated hosts (Jones et al. (1990) Nature 347:188–189; Jones et al. (1989) Blood 73:397–401), heterogeneity in transplantation potential appears to exist even within subpopulations of radioprotective cells. This has been demonstrated with serial bone marrow transplantations. The long-term repopulating ability of the grafts are lost with serial transfers, while a cell population survives which contributes to short-term reconstitution (Jones et al. (1989) supra). Further support for the concept that both short-term and long-term reconstituting stem cell populations exist have been derived from studies in which isoenzyme analysis and retroviral gene marking of hematopoietic cells have been utilized to track the fate of stem cells. A mathematical analysis of correlations and variances of donor reconstitution with isoenzyme variants in lethally irradiated mice indicates that a large number of multi-lineage clones are active immediately after reconstitution but rapidly decline, with the majority being inactive 12 weeks post-transplantation (Harrison & Zhong (1992) Proc. Natl. Acad. Sci. USA 89:10134–10138; Harrison et al. (1993) Exp. Hematol. 21:206–219). These observations indicate the existence of a population of cells with multi-lineage short-term engrafting potential in donor murine bone marrow. Similar observations have been made in a large animal transplantation model, where isoenzyme differences have indicated the contribution of multiple clones to short-term engraftment followed by sustained contributions by relatively few stem cell clones (Abkowwitz et al. (1990) Proc. Natl. Acad. Sci. USA 87:9062–9066). These findings have been confirmed by an elegant analysis of clonal development after transplantation with retrovirally marked stem cells (Jordan et al. (1990) Cell 61:953; Capel et al. (1990) Blood 75:2267).

The Hox family of homeobox genes are defined by the presence of a conserved 180 nucleotide sequence called the homeobox. Hox homeobox genes are related by the presence of a conserved 60-amino acid sequence that specifies a helix-turn-helix DNA-binding domain (Levine & Hoey (1988) Cell 55:5370540). Increasing evidence points to Hox homeo box genes as playing important lineage-specific roles throughout life in a variety of tissues including the hematopoietic system (for a review, see Lawrence & Largman (1992) Blood 80:2445–2453). In mammals, 38 Hox genes are found in four clusters (Boncinelli et al. (1989) Genome 31:745–756) referred to as A, B, C, and D (Scott (1992) Cell 71:551–553). During embryogenesis, the Hox genes exhibit a site and time-specific pattern of expression that correlates with their respective chromosomal position (referred to as spatial and temporal colinearity).

SUMMARY OF THE INVENTION

The invention features a stem cell modified to express an exogenous HOX gene. Expression of the exogenous HOX gene results in enhanced ability of the modified stem cell to generate expanded populations of pluripotent stem cells. When the modified stem cell is a hematopoietic stem cell, the expanded population of stem cells is characterized by the capacity to undergo substantial self-renewal and the ability to give rise to all hematopoietic cell lineages. Further, the expression of the HOX gene does not alter the normal proportion of mature blood cells or the commitment to specific blood cell lineages obtained with nonmodified stem cells.

In a preferred embodiment, the stem cell is a hematopoietic stem cell. In a more specific embodiment, the hematopoietic stem cell is a human hematopoietic stem cell expressing the cell surface marker CD34.

The HOX gene useful in the invention is any HOX gene which results in enhancement of stem cell capacity to undergo substantial self-renewal and the ability to give rise to all hematopoietic cell lineages. Preferably, the HOX gene inserted into the stem cell of the invention is a member of the HOXA or HOXB clusters; more preferably, the gene is HOXB4.

The stem cell of the invention may be modified by any means known to the art which results in stable integration and expression of an HOX gene in the modified cell and its progeny. Preferably, the stem cell of the invention is modified by transfection with a retroviral vector containing the HOX gene.

The invention features a method of expanding a population of stem cells by modifying a stem cell to express an exogenous HOX gene. The resulting expanded cell population is characterized by the capacity to undergo substantial self-renewal and the ability to give rise to all hematopoietic cell lineages. The expanded population gives rise to mature blood cells in the same or similar proportions resulting from the expansion of nonmodified stem cells. Still further, when transplanted into a recipient subject, the expanded population of stem cells restore hematopoietic capability to a subject without the development of leukemia.

The ability of HOX to expand a population of long-term repopulating cells which retain the ability to give rise to all hematopoietic cell lineages in normal proportions and which are not accompanied by development of leukemia is therapeutically useful. Accordingly, the invention features a therapeutic method for restoring hematopoietic capability to a human subject. Stem cells are recovered from a patient, modified and expanded in vitro, and returned to the subject, resulting in restoration of hematopoietic capability to the subject.

In the gene therapy aspect of the invention, hematopoietic stem cells are removed from a subject, transduced in vitro with a vector containing a HOX gene and a therapeutic gene, and returned to the subject either before or after in vitro expansion of stem cells having the capability of substantial self-renewal and ability to give rise to all hematopoietic cell lineages. These modified stem cells and their progeny will express the therapeutic gene product in vivo, and will preferentially repopulate the host system, thus providing sustained therapeutic benefit.

In addition to the advantages of stem cell expansion with generation of normal proportions of all the hematopoietic cell lineages, other advantages and features of the present invention will become apparent to those skilled in the art upon reading this disclosure.

DETAILED DESCRIPTION

Figure 1:
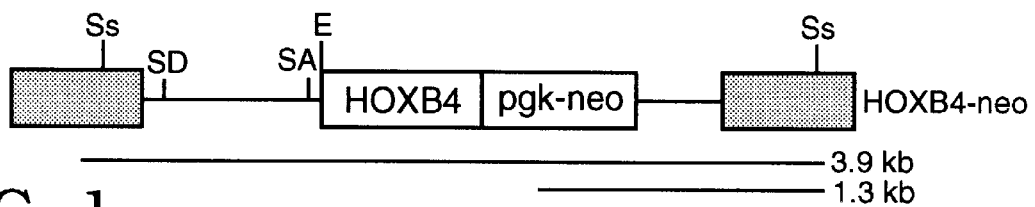
FIG. 1 is a diagrammatic representation of the HOXB4-neo viral construct. Expected size of the full-length viral transcripts and also those initiated from the PGK promoter are shown. SD and SA denote splice donor and splice acceptor sites. Alternate transcripts derived from these sites are not shown. Restriction sites indicated are EcoRI (E) and SstI (Ss).

Before the present invention and methods for using same are described, it is to be understood that this invention is not limited to the particular cell lines, HOX genes, or methodology described. It is also to be understood that the terminology used herein is for the purpose of describing particular embodiments only and is not intended to be limiting since the scope of the present invention will be limited only by the appended claims.

It must be noted that as used in this specification and the appended claims, the singular forms "a", "an" and "the" include plural references unless the context clearly dictates otherwise. Thus, for example, reference to "a stem cell" includes a plurality of cells, including mixtures thereof, and reference to "HOXB4" includes other HOX genes with the same biological effect.

Unless defined otherwise, all technical and scientific terms used herein have the same meaning as commonly understood by one of ordinary skill in the art to which this invention belongs. Although any methodology and materials similar or equivalent to those described herein can be used in the practice or testing of the present invention, the preferred methods and materials are now described. All publications mentioned herein are incorporated here in by reference for the purpose of disclosing and describing the particular materials and methodologies for which the reference was cited in connection with.

Definitions

By the term "stem cell" is meant a pluripotent cell capable of self-regeneration when provided to a subject in vivo, and give rise to lineage restricted progenitors, which further differentiate and expand into specific lineages. As used herein, "stem cells" includes hematopoietic cells and may include stem cells of other cell types, such as skin and gut epithelial cells, hepatocytes, and neuronal cells. Stem cells includes a population of hematopoietic cells having all of the long-term engrafting potential in vivo. Preferable, the term "stem cells" refers to mammalian hematopoietic stem cells; more preferably, the stem cells are human hematopoietic stem cells.

The terms "long-term repopulating stem cell" and "CRU" are used interchangeably to mean long lived stem cells capable of self-renewal and of giving rise to all hematopoietic cell lineages. For use in the present invention, a highly enriched stem cell population is preferred. An example of an enriched stem cell population is a population of cells which have been selected by expression of the CD34 surface marker, lack of expression of lineage specific markers (Lin$^-$), and which demonstrate selective enrichment of primitive pluripotent cells by functional assays, such as the in vitro initiating cell assay (LTCIC) (Sutherland et al. (1990) Proc. Natl. Acad. Sci. 87:3584–3588) or the in vivo CRU assay described below.

By "stem cell proliferation gene" is meant an exogenous gene which is incorporated into the stem cell genome and the expression of which results in enhanced proliferative potential of stem cells to generate a population of pluripotent or long-term repopulating stem cells which give rise to all hematopoietic cell lineages. Expansion may occur in vitro (i.e., prior to transplantation) and/or in vivo (i.e., enhanced regeneration of stem cell pools after transplantation). The stem cell proliferation gene useful in the invention is transplantable, able to restore hematopoietic capability to a mammal upon transplantation, and does not result in leukemogenesis in the transplanted subject. Preferably, the stem cell proliferation gene of the invention is HOX; more preferably, the gene is HOXB4.

By the term "modified stem cell" is meant a stem cell into which exogenous genetic material has been operatively incorporated into its genome. The modified stem cell is characterized by an enhanced ability to undergo self-renewal as compared to an unmodified stem cell. Preferably, the modified stem cell of the invention has a stably incorporated stem cell proliferation gene, expression of which results in a 10- to 100-fold expansion of a pluripotent stem cell population. More preferably, the stably incorporated stem cell proliferation gene results in a 50- to 100-fold expansion of a pluripotent stem cell population. The stem cell of the invention may be modified by a variety of means known to the art, including by introduction of exogenous genetic material by retroviral infection by liposome-mediated gene transfer, or adeno-associated viral vectors.

Stem cells may be isolated from any known human source of stem cells, including bone marrow, both adult and fetal, mobilized peripheral blood and umbilical cord blood. Initially, bone marrow cells may be obtained from a source of bone marrow, including ilium (e.g. from the hip bone via the iliac crest), tibia, femora, spine, or other bone cavities. Other sources of stem cells include embryonic yolk sac, fetal liver, fetal spleen, and fetal para-aortic region (AGM region).

For isolation of bone marrow, an appropriate solution may be used to flush the bone, including saline solution, supplemented with fetal calf serum (FCS) or other naturally occurring factors, in conjunction with an acceptable buffer at low concentration, generally from about 5–25 mM. Convenient buffers include HEPES, phosphate buffers and lactate buffers. Otherwise bone marrow may be aspirated from the bone in accordance with conventional techniques well known to those skilled in the art.

Methods for mobilizing stem cells into the peripheral blood are known in the art and generally involve treatment with chemotherapeutic drugs, e.g, cytoxan, cyclophosphamide, VP-16, and cytokines such as GM-CSF, G-CSF, or IL-3, or combinations thereof. Typically, apheresis for total white cells begins when the total white cell count reaches 500–2000 cells/$\mu$l and the platelet count reaches 50,000/$\mu$l. Daily leukapheris samples may be monitored for the presence of CD34$^+$ cells to determine the peak of stem cell mobilization and, hence, the optimal time for harvesting peripheral blood stem cells.

The cells responsible for reconstituting hematopoiesis in humans receiving a bone marrow transplant reside in a subset of cells expressing the CD34 antigen (CD34$^+$) (Berenson et al. (1991) Blood 77:1717–1722). This fraction of cells can be further subdivided based on multiple antigen characteristics (Lansdorp et al. (1990) J. Exp. Med. 172:363–366; Verfaille et al. (1990) J. Exp. Med. 172:509–520; Briddell et al. (1992) Blood 79:3159–3167) including the lack of lineage specific markers (Lin$^-$) (Baum et al. (1992) Proc. Natl. Acad. Sci. USA 89:2804–2808; Craig et al. (1993) J. Exp. Med. 177:1331–1342; Murray et al. (1990) Blood Cells 20:364–370; Murray et al. (1995) Blood 85:468). Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the viability of the fraction to be collected.

The use of separation techniques include those based on differences in physical (density gradient centrifugation and counter-flow centrifugal elutriation), cell surface (lectin and antibody affinity), and vital staining properties. Procedures for separation may include magnetic separation, using antibody-coated magnetic beads, affinity chromatography, cytotoxic agents joined to a monoclonal antibody or used in conjunction with a monoclonal antibody, including complement and cytotoxins, and "panning" with antibody attached to a solid matrix or any other convenient technique. Techniques providing accurate separation include flow cytometry which can have varying degrees of sophistication, e.g., a plurality of color channels, low angle and obtuse light scattering detecting channels, impedance channels, etc.

A large proportion of the differentiated cells may be removed by initially using a relatively crude separation, where the major populations of mature cells, such as lymphocytes, granulocytes, monocytes, megakaryocytic, mast cells, eosinophils, platelets, and basophils. Usually, at least about 70 to 90 percent of the hematopoietic cells will be removed.

The compositions comprising stem cells can be tested for the ability to produce myeloid cells and lymphoid cells by methods known to those skilled in the art.

HOXB4 Expansion of Pluripotent Stem Cells

It has been established that HOXB4 and several other HOXA and HOXB genes are preferentially expressed in the most primitive purified subpopulations of CD34$^+$ bone marrow cells. The present disclosure provides in vitro and in vivo evidence demonstrating that overexpression of HOXB4 has profound effects on the regenerative potential of long-term in vivo repopulating HSCs, as well as on the proliferation of intermediate types of hematopoietic progenitor cells, including both lymphoid (pre-B) and myeloid-restricted populations. Further, this enhancement of primitive progenitor cell amplification does not lead to leukemia and is not translated into an altered output of any type of mature blood cells or an altered commitment to any specific blood cell lineage.

Previous studies have shown that even after a single transplantation, the repopulating competence of unmodified regenerated bone marrow cells is reduced ~10-fold (Harrison (1982) J. Exp. Med. 156:1767–1779; Harrison et al. (1990) J. Exp. Med. 172:431–437). The reasons for the loss in repopulating competence is not known, although it has been hypothesized that the sustained proliferative stress imposed on at least some of these cells during the early phase of regeneration of the system may result in a decline in their probability of self-renewal in subsequent divisions.

Expression of a large number of HOXA, HOXB, and HOXC (but not HOXD) genes in various hematopoietic cell lines of human origin has been reported (Lawrence & Largman (1992) supra). These observations are consistent with the possibility that Hox gene products participate in the processes of HSC commitment and differentiation. Support for this concept is provided by studies indicating a correlation between the expression of specific Hox genes and the phenotype of different human hematopoietic cell lines. For example, HOXB3 has shown specificity of expression in lines showing erythroid features (Magli et al. (1991) Proc. Natl. Acad. Sci. 88:6348–6352; Matthews et al. (1991) Blood 78:2248–2252), and HOXA10 has shown a similar association with cells exhibiting myeloid properties (Lowney et al. (1991) Nucleic Acids Res. 19:3443–3449). Involvement of Hox genes in the regulation of proliferation of primary hematopoietic cells has also been reported (Perkins & Cory (1993) EMBO J. 12:3835–3846; Care et al. (1994) Mol. Cell. Biol. 14:4872–4877). Observed differences in the pattern of expression of Hox genes among the major subtypes of human leukemia (Celetti et al. (1993) Int. J. Cancer 53:237–244; Lawrence et al. (1995) Exp. Hematol. 23:1160–1166) suggest that they may also play a role in leukemogenesis.

Recent work from this laboratory has shown that most HoxA and HoxB cluster genes are expressed in the small fraction of normal human bone marrow cells that are CD34$^+$ (<4%; Civin et al. (1984) J. Immunol. 133:157–165) and contain most if not all hematopoietic progenitors (Sauvageau et al. (1994) Proc. Natl. Acad. Sci. 91:12223–12227, herein specifically incorporated by reference). Purification of this CD34+ fraction into three functionally defined distinct subpopulations: population I, CD45$^+$RA$^-$CD71$^-$, enriched for primitive pluripotent cells (LTCIC); population IIM, CD45$^{+RA+}$CD71$^-$, enriched for myeloid progenitors (CFU-GM); and population IIIE, CD45$^+$RA$^-$CD71$^+$, enriched for erythroid progenitors (BFU-E). RT-PCR-based analysis of Hox gene expression in these cells revealed two patterns of expression: one in which the level of expression of a given Hox gene (e.g., HOXA10, HOXB9, HOXC8) was essentially invariant in the different subpopulations, and the other in which the expression level was much higher (up to 40-fold) in subpopulations containing the most primitive hematopoietic cells (e.g., HOXB3, HOXB4). No gene was found to be up-regulated in the more mature CD34$^+$ cell subpopulations. Moreover, comparison of the levels of expression of selected Hox genes in CD34$^+$ and CD34$^-$ cells showed that Hox gene expression was higher in CD34$^+$ cells and lower (or undetectable) in the CD34$^-$ cells. Together, these data support the idea that Hox genes undergo down-regulation of expression with hematopoietic differentiation, and that some genes, such as HOXB3 and HOXB4, are almost exclusively expressed in the most primitive bone marrow cells.

The experiments described below were conducted to determine whether Hox gene expression has a role in determining primitive hematopoietic cell properties. Murine bone marrow cells were engineered to express HOXB4, and the effect of overexpression of HOXB4 on the subsequent behavior of these cells and their progeny in vitro and in vivo determined.

In an effort to achieve increased and persistent expression of HOXB4 in primitive hematopoietic cells, the human HOXB4 cDNA (SEQ ID NO:1) was introduced into murine bone narrow cells by retroviral-mediated gene transfer. The human HOXB4 cDNA was chosen on the basis of its availability and derivation from a hematopoietic tissue (Piverali et al. (1990) Differentiation 45:61–69, herein specifically incorporated by reference). Of the 361 amino acids found in the HOXB4 protein, only 9 are divergent between human and mouse and none of these occur within the homeo domain. This high degree of similarity (97%) made it very likely that the murine and human HOXB4 would be interchangeable (Bachiller et al. (1994) EMBO J. 13:1930–1941).

Figure 2:
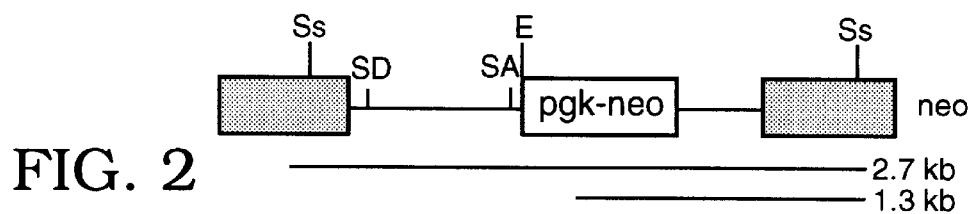
FIG. 2 is a diagrammatic representation of the neo provirus. Expected transcripts and identification of splice sites are as described in the legend to FIG. 1.

The HOXB4 cDNA (SEQ ID NO:1) (Piverali et al. (1990) Differentiation 45:61–69) was inserted into the murine stem cell virus (MSCV) retroviral vector 5' to a phosphoglycerate kinase promoter (PGK)-driven neo gene such that HOXB4 expression was driven from the promoter-enhancer sequences contained within the viral long terminal repeat (LTR) (FIG. 1) (neo vector shown in FIG. 2) (Example 1). The LTR sequences of MSCV were derived from a myeloproliferative sarcoma virus modified to show enhanced activity in embryonic stem cell lines and were therefore expected to have similar activities in primitive hematopoietic cells (Grez et al. (1990) Proc. Natl. Acad. Sci. 87:9202–9206; Hawley et al. (1992) supra). High titer polyclonal viral producer cells were generated from the GP+E-86 ecotropic packaging cell line using standard methods. Integrity of the HOXB4-neo retrovirus was verified by Northern blot analysis to detect the expected mRNA in viral producer cells and by Western blot analysis to detect HOXB4 protein in transduced murine (FDC-P1) and human (K562) hematopoietic cell lines.

Figure 3:
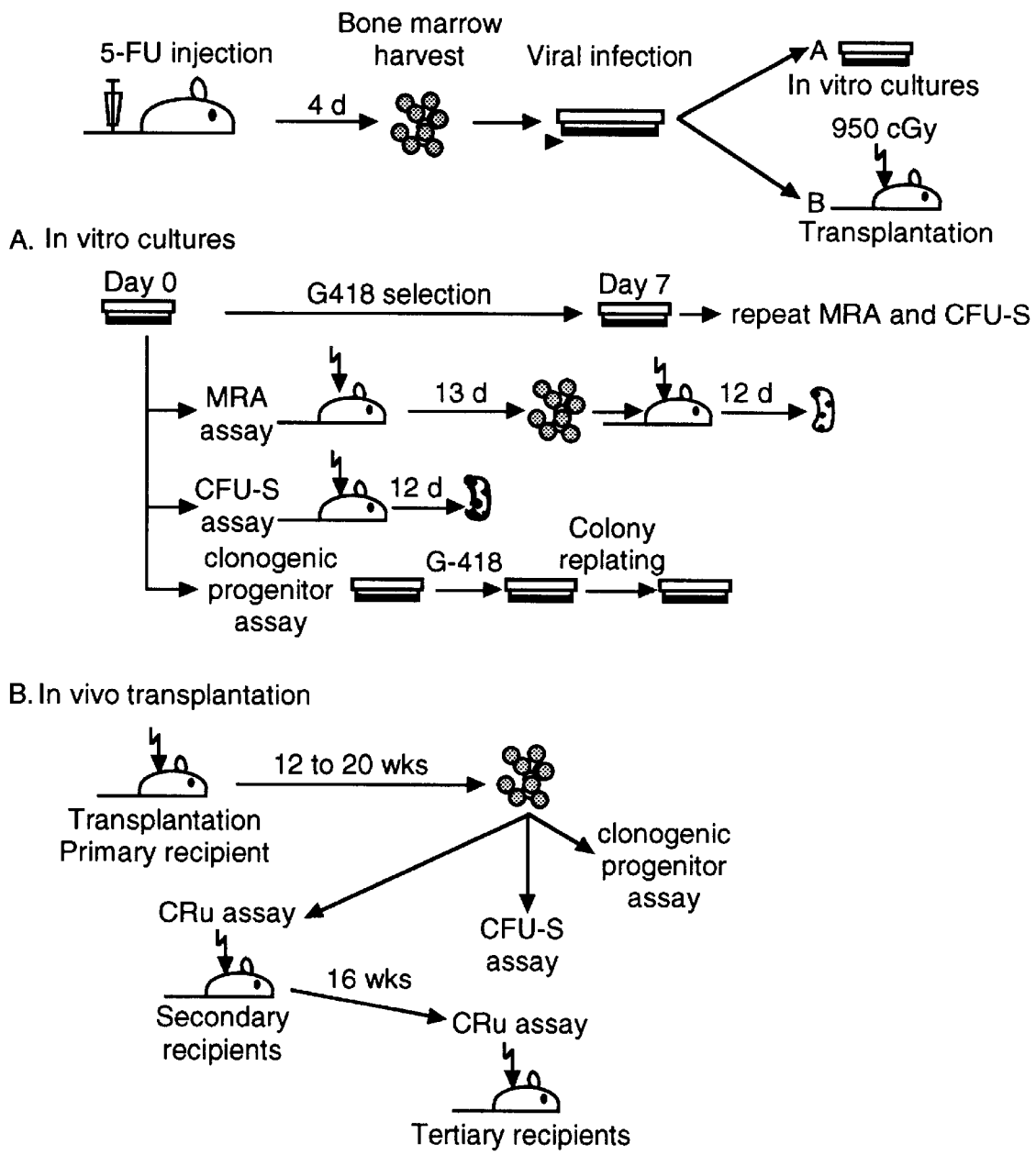
FIG. 3 is a schematic flow chart of the experimental strategy used to study the effects of HOXB4 overexpression on the behavior of primitive hematopoietic cells and their progeny.

The experimental strategy used to study the effects of HOXB4 overexpression on the behavior of primitive hematopoietic cells and their progeny is depicted schematically in FIG. 3. Briefly, bone marrow cells obtained from mice treated with 5-fluorouracil (5-FU) were co-cultivated with HOXB4 or control neo viral producer cells, and in vivo transplantation and in vitro culture experiments performed. In vitro cultures were used to determine the effect of HOXB4 on the number and types of cells produced, as assessed by clonogenic progenitor, colony forming units (CFU-S), marrow repopulating ability (MRA) assays. These assays measure cells with increasing degress of primitiveness (MRA>CFU-S>clonogenic progenitors). In vivo transplantation studies included clonogenic progenitor and CRU assays in stem cells recovered 12–20 weeks post-transplantation from primary recipients, and CRU assays performed with cells recovered 16 weeks post-transplantation from secondary recipients. The CRU assay provides a rigorous and quantitative measure of cells with long-term myeloid and lymphoid repopulation in vivo.

Figures 4, 5:
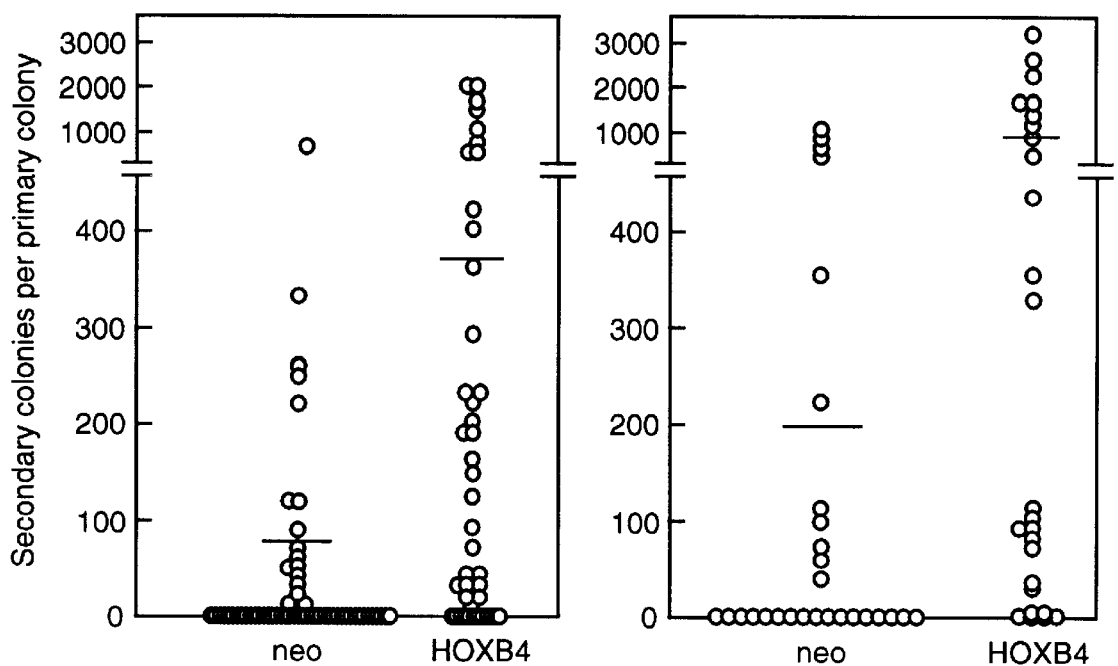
FIG. 4 is a diagram showing the effect of HOXB4 overexpression on the ability of individual methylcellulose colonies to form secondary colonies upon replating. Isolated HOXB4- or neo-transduced colonies from primary cultures were randomly picked at 7 days of G418 selection in methylcellulose cultures. Each dot represents the number of secondary colonies generated from each primary colony that was picked and replated in the same culture conditions. The calculated mean number of secondary colonies obtained per primary colony is indicated by the broad dash. The difference was significant at the P<0.005 level (Student t-test).
FIG. 5 is a diagram showing the effect of HOXB4 overexpression on the ability of individual methylcellulose colonies to form secondary colonies upon replating. Isolated HOXB4- or neo-transduced colonies from primary cultures were randomly picked at 11 days of G418 selection in methylcellulose cultures. Each dot is as described in the legend to FIG. 3A. The difference was significant at the P<0.005 level (n=2; Student t-test).

Initial studies examined possible effects of HOXB4 overexpression in committed clonogenic progenitor cells detected by their ability to give rise to myeloid, erythroid, or myeloid/erythroid colonies in semisolid culture (Example 2). In vitro cultures of bone marrow cells included cells co-cultivated with virus producing cells or harvested from reconstituted transplant animals. Gene transfer efficiencies, as judged by the percentages of G418-resistant clonogenic progenitors and the proportion of different colony types, were similar for HOXB4 or neo-infected cells (58–70%). However, HOXB4-infected cells gave rise to significantly greater numbers of large granulocyte-macrophage colonies than that observed in control cultures (41% v. 16%, respectively), supporting enhanced proliferative capacity of cells at a relatively late step in development. Further, the proliferative capacity of the HOXB4-infected cells was greater than neo-infected cells, as evidenced by their ability to generate 2- to 3-fold increase in secondary colonies (FIGS. 4 and 5).

On the basis of the observed increase in the proliferative ability of progenitors with in vitro clonogenic potential following their transduction with HOXB4, additional experiments were performed to determine whether similar effects on the behavior of earlier cells detectable as day-12 CFU-S or as cells with marrow repopulating ability (MRA) could be seen (Example 3). For these studies, infected bone marrow cells were assayed for CFU-S and MRA content immediately after the period of co-cultivation with viral producer cells and again after an additional 7 days in liquid culture in the presence of 1.4 mg/ml of G418. The CFU-S content of recovered cells assessed immediately after co-cultivation (day 0) (FIG. 6) were similar for HOXB4 or neo control. However, after maintenance in liquid culture for 7 days (day 7) (FIG. 6), the CFU-S content of cultures initiated with neo-transduced cells was <1% of input, while the CFU-S content of cultures initiated with HOXB4-transduced cells increased to 200%–500% of input.

Figure 7:
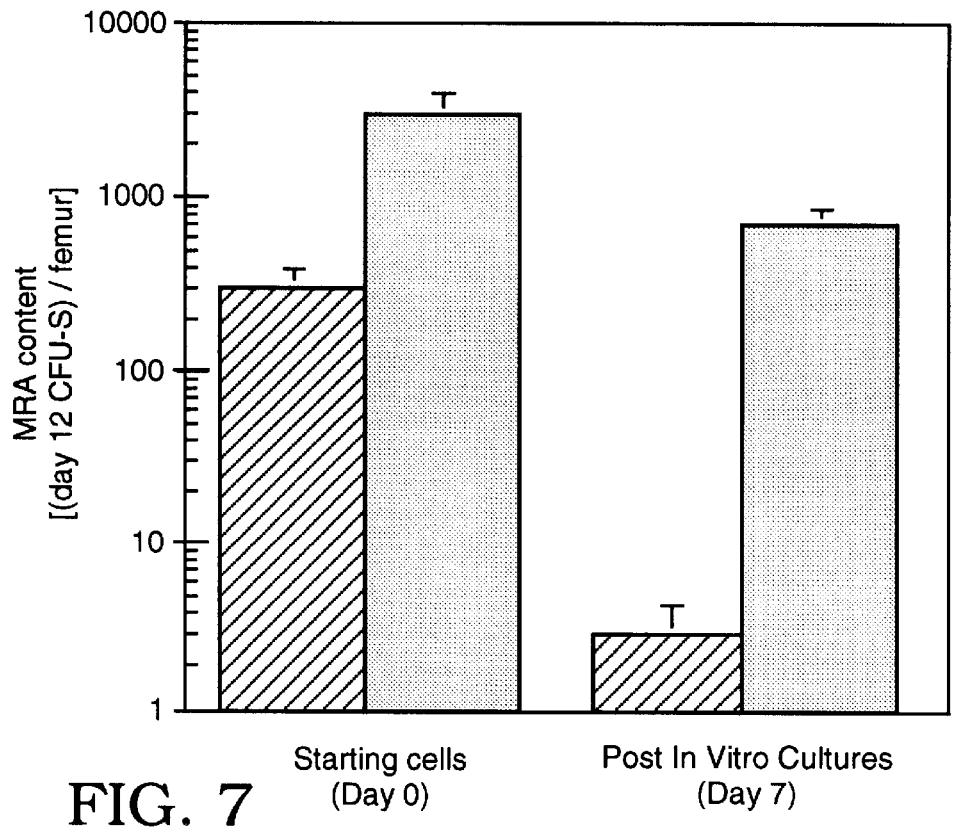
FIG. 7 is a bar diagram showing the effect of HOXB4 on cells with marrow repopulating ability (MRA). MRA was assayed by the content of day-12 CFU-S per femur present in recipients transplanted 13 days previously with HOXB4- (solid bar) or neo-transduced (hatched bar) bone marrow cells. The MRA of $2\times10^5$ cells was determined immediately after viral infections (day 0) or after their culture for 7 days. Results are mean±S.D. of day-12 CFU-S determined in a minimum of 10 recipients.

The MRA assay measured the ability of a test cell population to regenerate day-12 CFU-S in the bone marrow of a lethally irradiated recipient transplanted 13 days earlier. The cells thus detected share with HSC a resistance to cycle-active chemotherapeutic drugs (Hodgson & Brandley (1984) Exp. Hematol. 12:683–687) and are thought to be precursors of most CFU-S (Mauch & Hellman (1989) Blood 74:872–875). At day 0 of co-cultivation, MRA was 10-fold higher in recipients transplanted with HOXB4-infected cells relative to the neo control (FIG. 7). Following 7 days of liquid-culture (day 7), the MRA content of neo-transduced cells was undetectable, while that of HOXB4-transduced cells was >200-fold higher (FIG. 7). Thus, it appears that the marked (i.e., >2 log) reduction in day-12 CFU-S numbers that occurred when neo-transduced cells were maintained in vitro for 7 days was accompanied by a similar reduction in MRA. In contrast, HOXB4 overexpression reversed this decline leading to a net increase in CFU-S content and a near maintenance of MRA.

It has been reported previously that the CFU-S content of growth factor-stimulated post-5-FU-treated bone marrow cells decreased dramatically with time using similar culture conditions (Bernad et al. (1994) Br. J. Haematol. 87:6–17). The results reported here with neo-transduced cells are consistent with this report (i.e., there was a decrease of ~2 log in the number of CFU-S at the end of 7 days in culture). However, the CFU-S content of the cultures initiated with HOXB4-transduced cells expanded by two-to five-fold during the same period. Similar differences in the recovery of day 12 CFU-S after in vitro culture was observed in comparisons of non-5-FU-treated bone marrow harvested from mice reconstituted previously with HOXB4- versus neo-transduced marrow (data not shown). To what extent this difference reflects effects on survival versus self-regeneration and/or recruitment from earlier cells remains unresolved at this time. Although the exact mechanisms responsible for this phenomenon are currently unclear, the magnitude of the differences observed suggests that this system is useful as an experimental tool for the identification of HOXB4 target genes.

Expansion of hematopoietic precursors without a concomitant increase in the number of peripheral blood cells has not been observed previously when the effects of overexpression of various hematopoietic growth factors have been studied in a similar model (Johnson et al. (1989) EMBO J. 8:441–448; Wong et al. (1989) Mol. Cell. Biol. 9:798–808; Chang & Johnson (1991) Exp. Hematol. 19:602–607; Tanaka et al. (1991) Blood 77:2597–2602; Hawley et al. (1992) Oncogene 9:1–12; Fraser et al. (1993) J. Immunol. 151:2409–2418). In most of these reports, it was found that overexpression of the cytokines studied resulted in an increase in the number of peripheral blood cells but that the content of bone marrow clonogenic progenitors was either unchanged or, in some cases, diminished. Interestingly, overexpression of the nonclustered homeo domain-containing gene TCL-3 (previously called HOX11) (Hawley et al. (1994) supra) or HoxB8 (Perkins & Cory (1993) EMBO J. 12:3835–3846) in murine bone marrow cells was also found to have proliferative effects. In both studies, generation of cell lines from transduced bone marrow cells was observed with high frequency in the presence of interleukin-3 (IL-3). In contrast, efforts to generate cell lines in similar conditions (i.e., high IL-3 concentrations) were unsuccessful with HOXB4 (data not shown). Effects on earlier stem cell populations were not directly assessed in the two earlier studies. Interestingly, mice transplanted with HoxB8-transduced marrow cells showed increased levels of bone marrow and splenic clonogenic progenitors at 3 months post-transplantation. Because Hox genes found at the 3' end of the Hox clusters (e.g., HOXB4) are thought to be regulators of more 5' Hox genes (e.g., HoxB8, etc.) (Faiella et al. (1994) Proc. Natl. Acad. Sci. 91:5335–5339), it is possible that some of the effects described in the present disclosure may involve activation of 5' genes. A significant proportion of mice transplanted with HoxB8-transduced cells, however, developed leukemic transformation at ~7 months post-transplantation. By contrast, the effects observed with HOXB4 are not accompanied by leukemic transformation.

The fact that clonogenic progenitors transduced with HOXB4 also replated much better in vitro than those transduced with neo provides evidence that this gene can also directly influence the proliferative capacity of later progenitors and that expansion of these later types of hematopoietic cells is not secondary to the expansion of CRUs. The absence of any perturbation in the proportions of different types of lineage-restricted clonogenic progenitors produced in vivo or the number of mature blood cells present in the circulation of mice repopulated with HOXB4-transduced cells provides evidence that this gene can influence stem cell self-renewal events in the absence of effects on lineage commitment or terminal differentiation. This finding is consistent with the concept recently proposed by Fairbain et al. (1993) Cell 74:823–832, based on studies with the FDCP-mix cell line that self-renewal and commitment processes may not necessarily be linked at the molecular level. Together with the initial observation showing preferential expression of HOXB4 in the most primitive bone marrow cell populations (Sauvageau et al. (1994) supra), the data presented herein suggests that the absolute level of HOXB4 can be a critical determinant of HSC proliferative ability. Interestingly, it was shown recently that inhibition of HOXB4 expression using antisense oligonucleotides in peripheral blood progenitors compromised the proliferation of these cells (Carè et al. (1994) supra; Giampaolo et al. (1994) Blood 84:3637–3647).

To assess the effects of HOXB4 overexpression on hematopoietic cells maintained for prolonged periods in vivo, HOXB4- or neo-transduced bone marrow cells were transplanted immediately after infection into lethally irradiated syngeneic recipients and reconstitution of hematopoietic populations evaluated (Example 4). Consistent with earlier studies, it was found that the pool of long-term repopulating stem cells (CRU) regenerated in recipients of neo-transduced cells did not recover beyond a level equivalent to 3%–6% of that characteristic of normal mice despite the return to normal levels of bone marrow cellularity and clonogenic progenitors and frequencies.

A different picture emerged in mice transplanted with marrow overexpressing HOXB4. Here, CRU numbers recovered to a level that was 1.4-fold higher than the normal value and 47-fold higher than that observed in animals transplanted with neo-transduced marrow.

The pre-B and myeloid clonogenic progenitor content of bone marrow 12 weeks after transplantation was 2-fold higher relative to that in neo-infected cell recipients (Table 1). 20 weeks after transplantation, a 5- and 32-fold increase was seen in bone marrow and splenic clonogenic progenitor numbers, respectively, in HOXB4-transduced relative to neo-transduced cell recipients (Table 1).

To further determine the effect of HOXB4 overexpression on the expansion of the earliest hematopoietic cells, their number was quantified following serial transplantation by limiting dilution analysis of secondary recipients using the CRU assay (Example 5). Serial transplantation studies were conducted in which as few as five CRUs transplanted into secondary recipients were shown to be capable of regenerating a significant CRU pool not demonstrably compromised in repopulating ability (Table 2). In contrast, serial transplantation compromised even further the ability of neo-transduced and/or nontransduced CRUs to regenerate CRUs in successive recipients.

Figure 8:
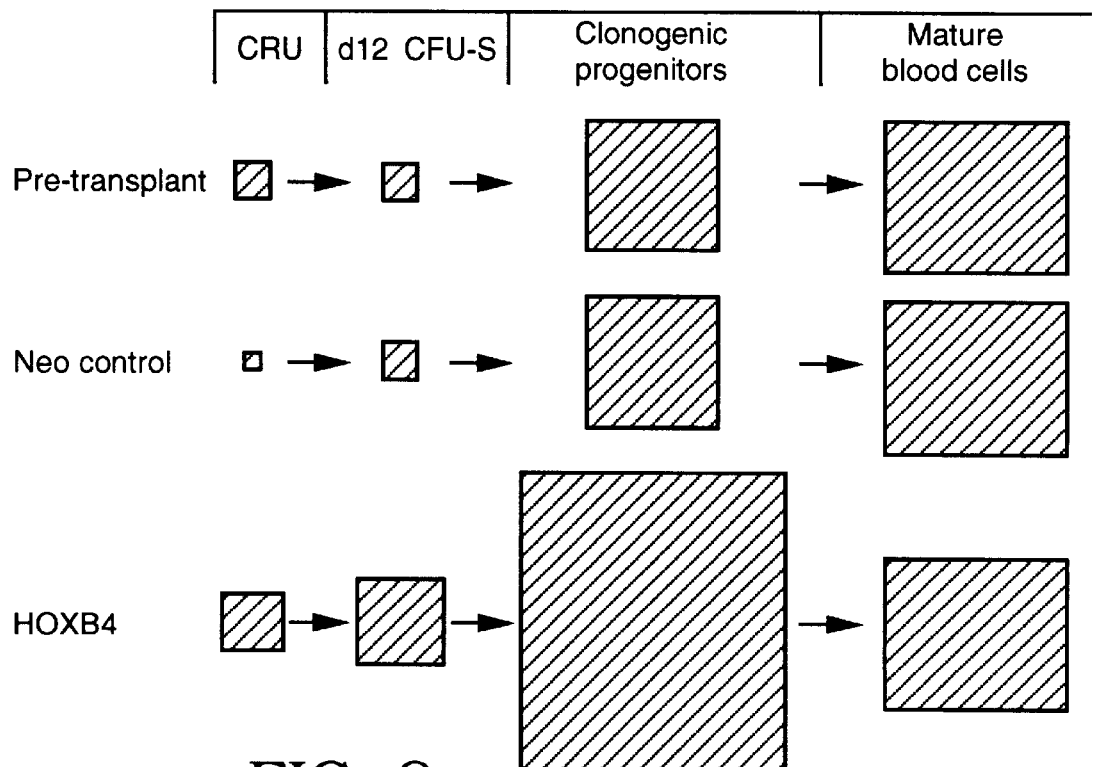
FIG. 8 is a schematic depiction of the sizes of various hematopoietic populations reconstituted in primary recipients of HOXB4- or neo-transduced bone marrow cells compared to normal (unmanipulated) mice ("pre-transplant"). Except for the boxes representing the peripheral blood cells that were equivalent in numbers, the surface area of each box is drawn to scale to indicate the relative frequencies of the cell populations.

The results presented herein establish that HOXB4 is a key regulator of proliferative potential of long-term repopulating HSCs and that overexpression of this gene does not override the regulatory mechanisms involved in lineage determination or in the control of end cell output. The engineered overexpression of HOXB4 in the in vivo murine model was found to have profound effects on the proliferation of long-term in vivo repopulating HSCs and to a lesser esten on the proliferation of intermediate types of hematopoietic progenitor cells including both lymphoid (pre-B)- and myeloid-restricted populations (FIG. 8). Nevertheless, amplification of the primitive progenitor cell population did not lead to leukemia or alter output of any type of mature blood cell or commitment to any specific blood cell lineage. These findings demonstrate that it is possible to reverse the decline of HSCs that normally occurs during regeneration of the hematopoietic system after bone marrow transplantation resulting in a dramatic expansion of genetically modified HSCs in vivo.

Therapeutic Use of HOXB4-Induced Enhancement of Stem Cell Proliferative Capacity The present invention is based on the discovery that the expression of HOXB4 has unique and unexpected effects on mammalian stem cells. As established by the evidence provided herein, long-term repopulating stem cells engineered to overexpress HOXB4 generate an expanded population of cells with the ability to undergo substantial self-renewal and the ability to give rise to all hematopoietic cell lineages. The effect of HOXB4 on cell expansion results in no discernable effect on differentiation. Additionally, HOXB4 appears to promote the survival of stem cells in in vitro culture.

The subset of primitive hematopoietic cells shown herein to be affected by HOXB4 are long-term repopulating or pluripotent stem cells, characterized by the ability to give rise to cells which retain the capability of self-renewal, and to proliferate and differentiate into cells of all hematopoietic lineages.

Use of HOXB4 Expression for Expansion of Long-Term Repopulating Cell Populations. The ability of HOXB4 expression to enhance the proliferative capacity of a primitive stem cell subpopulation without loss of the pluripotent capacity has important clinical implications for restoration of hematopoietic capability in subjects in which hematopoietic capability is lost or threatened. Accordingly, the invention features a method for endowing primitive marrow cells with increased regenerative potential in vivo by modifying a stem cell to express an exogenous HOX gene. This potential may be exploited through in vitro cultures to expand stem cells and/or following in vivo transplantation where transduced cells have a competitive proliferative advantage, resulting in significantly greater reconstitution of the stem cell compartment. This is particularly useful for re-establishing hematopoietic capability in patients in which native hematopoietic function has been partially, substantially, or completely compromised. Stem cells from any tissue are removed from a subject, modified by insertion of a HOX gene, expanded in vitro by expression of the HOX gene, and returned to the subject with or without in vitro expansion. If necessary, the process may be repeated to ensure substantial repopulation of the stem cells. The expanded stem cell population returned to the subject retain pluripotent characteristics, e.g., self-renewal and ability to generate cells of all hematopoietic lineages. When in vitro expansion is desired, a combination of various cytokines can be utilized to ensure that the transduced cell population will include expanded numbers of progenitor cells and more mature cells of the various hematopoietic lineages (e.g., megakaryocytes, neutrophils) in addition to stem cells to provide a cell population that will provide both short-term and long-term repopulation potential.

Stems cells are preferably isolated from bone marrow or mobilized peripheral blood, and more preferentially from bone marrow. Expansion procedures are conducted by methods known to the art, and may be conducted either with or without stromal cells. Stromal cells may be freshly isolated from bone marrow or from cloned stromal cell lines. Such lines may be human, murine, or porcine. For clinical applications, it is preferred to culture the stem cells in the absence of stromal cells. Expansion may be conducted with a variety of cytokines and growth factors, e.g., FLT-3 or steel factor. Various in vitro and in vivo tests known to the art may be employed to ensure that the pluripotent capability of the stem cells has been maintained.

Use of HOX-Induced Enhancement of Stem Cell Proliferative Capacity in Gene Therapy. The effect of HOX gene expression on the expansion of a population of long-term repopulating stem cells is particularly important for providing human stem cells with one or more exogenous genes for gene therapy. Further, the ability to provide modified human pluripotent cells stem cells having the improved ability to compete in vivo results in the long-term repopulation of an individual with the modified cells and their progeny, which will express the desired gene product. By contrast, gene transfer into more mature hematopoietic cells, such as T cells, at best, provides only transient therapeutic benefit. For reviews of genetic modification of stem cells see Brenner (1993) J. Hematother. 2:7–17; Miller (1992) Nature 357:455–460; and Nienhuis (1991) Cancer 67:2700–2704.

While retroviral vectors may be used to genetically modify a population of human long-term repopulating stem cells, other methods may be used, such as liposome-mediated gene transfer or adeno-associated viral vectors. Retroviral vectors have been the primary vehicle due to the generally high rate of gene transfer obtained in experiments with cell lines, and the ability to obtain stable integration of the genetic material, which ensures that the progeny of the modified cell will contain the transferred genetic material.

Hematopoietic stem cells are removed from a human patient, and a population of long-term repopulating stem cells isolated. These cells may be optionally expanded prior to or after modification by transduction with a vector carrying the desired gene. The population of modified long-term repopulating stem cells are then restored to the human patient with or without in vitro expansion, for expression of the foreign gene. The patient may be treated to partially, substantially, or completely ablate the native hematopoietic capability prior to restoration of the modified stem cells. Preferably, after completion of the treatment of the host, the modified stem cells may then be restored to the host to provide for expression of the foreign gene. The methods of stem cell removal, host ablation and stem cell repopulation are known in the art. If necessary, the process may be repeated to ensure substantial repopulation of the modified stem cells.

Transduction may be accomplished by the direct co-culture of stem cells with producer cells, following the methods described below. For clinical applications, transduction by culturing the stem cells with viral supernatant alone or with purified viral preparations, in the absence of stromal cells, is preferred. Polycations, such as protamine sulfate, polybrene and the like, will generally be included to promote binding. Protamine sulfate and polybrene are typically used in the range of 4 $\mu$g/ml. Additionally, cytokines may also be added, including, e.g., IL-3, IL-6, LIF, steel factor (Stl) GM-CSF, G-CSF, MIP-1$\alpha$, and Flk2/Flt3, preferably including Stl. The factors employed may be naturally occurring or synthetic, e.g., prepared recombinantly, and preferably human.

To ensure that the stem cells have been successfully modified, PCR may be used to amplify vector specific sequences in the transduced stem cells or their progeny. In addition, the cells may be grown under various conditions to ensure that they are capable of maturation to all of the hematopoietic lineages while maintaining the capability, as appropriate, of the introduced DNA. Various in vitro and in vivo tests described above may be employed to ensure that the pluripotent capability of the stem cells has been maintained.

Gene Therapy Applications. Gene transfer into stem cells may be used to treat a variety of neoplastic, infectious or genetic diseases. For example, one may introduce genes that confer resistance to chemotherapeutic agents, thereby protecting the hematopoietic cells, allowing higher doses of chemotherapy and thereby improving the therapeutic benefit of treatment. For viral infections that primarily affect hematolymphoid cells, stem cells may be modified to endow the progeny with resistance to the infectious agent. In the case of human immunodeficiency virus (HIV), for example, specific antisense or ribozyme sequences may be introduced that interfere with viral infection or replication in the target cells. Alternatively, the introduced gene products may serve as "decoys" by binding essential viral proteins, thereby interfering with the normal viral life cycle and inhibiting replication.

Alternatively, stem cells may be modified to produce a product to correct a genetic deficiency, or where the host has acquired a genetic deficiency through a subsequent disease. The ability of HOXB4 to confer a competitive advantage in vivo to cells overexpressing HOXB4 demonstrated herein is an important feature in providing long-term corrective genetic therapy.

Expression of the transferred gene can be controlled in a variety of ways depending on the purpose of gene transfer and the desired effect. Thus, the introduced gene may be put under the control of a promoter that will cause the gene to be expressed constitutively, only under specific physiologic conditions, or in particular cell types. Examples of promoters that may be used to cause expression of the introduced sequence in specific cell types include Granzyme A and Granzyme B for expression in T-cells and NK cells, the CD34 promoter for expression in stem and progenitor cells, the CD8 promoter for expression in cytotoxic T-cells, and the CD11b promoter for expression in myeloid cells. Inducible promoters may be used for gene expression under certain physiologic conditions. The therapeutic benefit may be further increased by targeting the gene product to the appropriate cellular location, for example, the nucleus, by attaching the appropriate localizing sequences. In addition, by appropriate use of inducible promoters, expression of various protein products can be achieved in response to particular stimuli such as chemicals, chemo-attractants, particular ligands, and the like.

EXAMPLES

The following example are put forth so as to provide those of ordinary skill in the art with a complete disclosure and description of how to modify stem cells to express a gene which enhances stem cell self-renewal (e.g., an HOX gene), its use for expansion of pluripotent stem cells, and therapeutic methods of the present invention, and are not intended to limit the scope of what the inventors regard as their invention. Efforts have been made to ensure the accuracy with respect to numbers used (e.g., amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Animals. Mice used as recipients were 7- to 12-week old (C57Bl/cJ×C3H/HcJ)F$_1$[(B6C3)F$_1$], and those used as bone marrow donors (C57Bl/6Ly-Pep3b×C3H/HeJ)F$_1$[(PepC3) F$_1$] male and female mice bred and maintained in the animal facility of British Columbia Cancer Research Center from parental strain breeders originally obtained from Jackson Laboratories (Bar Harbor, Me.). (B6C30F$_1$ and (PepC3)F$_1$ mice are phenotypically distinguishable on the basis of allelic differences at the Ly5 locus: (B6C3)F$_1$ mice are Ly5.2 homozygotes and (PepC3)F$_1$ mice are Ly5.1/Ly5.2 heterozygotes. All animals were housed in microisolator cages and provided with sterilized food and acidified water.

Retroviral generation. The MSCV retroviral vector MSCV 2.1 was provided by Dr. R. Hawley (Sunnybrook Research Institute, Toronto, Canada). The HOXB4 cDNA region encompassing the complete coding sequence was isolated as a BamHI fragment from a plasmid (provided by Dr. E. Boncinelli, Ospedale S. Faffaele, Milan, Italy) and cloned upstream of the PGK-neo cassette at the XbaI site of MSCV 2.1 by blunt-end ligation using standard procedures (Davis et al. (1994b) in Basic Methods in Molecular Biology, Appleton and Lange, Norwalk, Conn.; pp. 350–355). Production of high-titer ecotropic helper-free recombinant retroviruses was carried out using standard procedures (Pawliuk et al. (1994) Blood 84:2868–2876) in the ecotropic GP+E-86 (Markowitz et al. (1988b) J. Virol. 62:1120–1124) and amphotropic GP+envAM12 (Markowitz et al. (1988a) Virology 167:400–406) packaging cell lines. The viral titers of the GP+E-86-MSCV2.1-PGK-neo and GP+E-86-MSCV2.1-HOXB4-PGK-neo (hereinafter "neo" and "HOXB4-neo", respectively) producer cells were $3\times10^6$ to $5\times10^6$ CFUs/ml and $3\times10^5$ to $5\times10^5$ DFUs/ml, respectively, as assessed by transfer of F418 resistance to NIH-3T3 cells (Cone & Mulligan (1984) Proc. Natl. Acad. Sci. 81:6349–6353). Absence of helper virus generation in the HOXB4-neo viral producer cells was verified by failure to serially transfer virus conferring G418 resistance to NIH-3T3 cells (Cone & Mulligan (1984) supra). The absence of helper virus in serum of mice transplanted with HOXB4-neo-transduced bone marrow was also confirmed using a rescue assay.

Cell lines. The ecotropic packaging cell line GP+E-86 and the amphotropic cell line Gp+envAM12 used to generate the recombinant retroviruses were maintained in HXM medium that consists of Dulbecco's modified Eagle medium (DMEM), 10% heat-inactivated (55° C. for 30 min) newborn calf serum (NCS) (GIBCO-BRL), 15 µg/ml of hypoxanthine (Sigma), 250 µg/ml of xanthine (Sigma), and 25 µg/ml of mycophenolic acid (Sigma). Virus-producing cells were maintained in HXM medium supplemented with 1 mg/ml of neomycin analog G418, and for the amphotropic cell line 200 µg/ml of hygromycine was added (Sigma). Twenty-four hours prior to harvest of viral supernatant or co-cultivated with bone marrow cells, virus producer cells were cultured in RPMI with 105 fetal calf serum (FCS) or DMEM with 10% NCS, respectively. Unless specified otherwise, all cultures were maintained at 37° C. in a humidified atmosphere of 5% $CO_2$ in air. All media, serum, and growth factors unless otherwise specified were obtained from StemCell Technologies Inc. (Vancouver, B.C., Canada).

Transplantation of retrovirally transduced bone marrow. Lethally irradiated 7- to 10-week-old $(B6C3)F^1$ (Ly5.2) mice (950 cGy, 110 cGy/min, $^{137}Cs$ gamma rays) were injected intravenously with $2\times10^5$ bone marrow cells derived from $(PepC3)F_1$ (Ly5.1/Ly5.2) immediately after co-cultivation of these cells with HOXB4-neo or neo viral producer cells. The levels of Ly5.1 donor-derived repopulation in recipients were assessed 12, 20, and 34 weeks post-transplantation by flow cytometric analysis of peripheral blood samples obtained by tail vein puncture (Rebel et al. (1994) Blood 83:128–136). In all animals, >86% of all the peripheral blood leukocytes were of donor Ly5.1 origin. At these same time points, peripheral blood cell counts and hematocrits were determined for some of these animals.

DNA and RNA analyses. Southern blot analyses to asses proviral integration were performed as reported previously (Pawliuk et al. (1994) supra) using standard techniques. High-molecular weight DNA was digested with SstI that cuts in the LTRs to release the proviral genome or with EcoRI that cuts the provirus once to release DNA fragments specific to the proviral integration sites. Total cellular RNA was isolated using TRIzol (GIBCO BRL) and separated using formaldehyde/agarose gel electrophoresis. The RNA was transferred to nylon membrane (Zeta-probe; Rio-Rad), prehybridized, hybridized, and washed as described (Davis est al. (1994a) in Basic Methods in Molecular Biology, supra, pp. 350–355). Probes used were a XhoI-SalI fragment of pMClneo (Thomas & Capecchi (1987) Cell 51:503–512), KpnI-MseI fragment of pSM(ER)-190 that releases the full-length erythropoietin receptor cDNA (provided by A. D'Andrea, Dana-Farber Cancer Institute, Boston, Mass.), and full-length HOXB4 cDNA labeled as described (Sauvageau et al. (1994) Proc. Natl. Acad. Sci. 91:1223–1227, herein specifically incorporated by reference).

Western analysis. To detect HOXB4 protein, FDC-P1 and K562 transfected cells were harvested and lysed in cracking buffer (1% SDS, 6M urea, 1% β-ME, 0.01M sodium phosphate, pH 7.2). Proteins (5 µg) were subjected to SDS-PAGE in a 12.5% gel and transferred to nitrocellulose membrane. Membranes were incubated with a mixture of two polyclonal antisera (1:5000 dilution for each) raised against peptides deduced from the amino-terminal and carboxy-terminal regions flanking the homeo domain of the HOXB4 protein, respectively (BAbCo, Richmond, Calif.), and incubation with secondary antibody was coupled to alkaline phosphatase. Each peptide antisera was shown previously to specifically detect HOXB4 expressed as a bacterial fusion protein.

Retroviral infection of primary bone marrow cells and hematopoietic cell lines. Bone marrow cells were obtained from $(PepC3)F_1$ (Ly5.1/Ly5.2) mice injected intravenously 4 days previously with 150 mg/kg body weight of 5-fluorouracil (5-FU) in phosphate-buffered saline, by flushing femurs and tibias with DMEM 2% FCS using a 21-gauge needle. Single-cell suspensions of $1\times10^5$ to $5\times10^5$ cells/ml were then cultured in a petri dish for 48 hr in DMEM containing 15% FCS, 10 ng/ml of human IL-6, 6 ng/ml of murine IL-3, and 100 ng/ml of murine Steel factor (Stl). All cells were then harvested and plated at $1\times10^5$ to $2\times10^5$ cells/ml in the above medium supplemented with 6 µg/ml of polybrene on viral producer cell monolayers irradiated (1500 cGy Xray) the same day at 80%–100% confluence. Cells were co-cultured for 48 hr with a medium change after 24 hr. Loosely adherent and nonadherent cells were recovered from the co-cultures by agitation and repeated washing of dishes with Hank's balanced salt solution containing 2% FCS. Recovered bone marrow cells were washed once and then counted using a hemocytometer. All growth factors were used as diluted supernatant from transfected COS cells prepared in the Terry Fox Laboratory.

Example 2

Clonogenic Progenitor Assays

For myeloid clonogenic progenitor assays, bone marrow cells from mice treated 4 days previously with 5-fluorouracil (5-FU) were co-cultivated with HOXB4 or control neo viral producer cells and 48 h post-infection were plated in methylcellulose cultures. Cells were plated on 35-mm petri dishes (Greiner, Germany) in a 1.1 ml culture mixture containing 0.8% methylcellulose in alpha medium supplemented with 30% FCS, 1% bovine serum albumin (BSA), $10^{-4}M$ β-mercaptoethanol (β-ME), 3 U/ml of human urinary erythropoietin (Epo), and 2% SCCM in the presence or absence of 1.4 mg/ml of G418. To ensure random colony selection in single colony replating experiments, cultures were also supplemented with 500 ng/ml of murine IL-3, which abrogates the size difference between colonies. Bone marrow cells harvested from the co-cultivation with virus producer cells or from reconstituted transplant animals were plated at a concentration of $2\times10^3$ cells/dish or $2\times10^4$ to $4\times10^4$ cells/dish, respectively. Spleen cells from animals transplanted with HOXB4-neo- or neo-transduced cells were plated $3 \times 10^5$ cells/dish, or $3 \times 10^6$, respectively. Colonies were scored on day 12 to day 14 of incubation as derived from granulocyte-macrophage (CFU-GM), burst forming unit-erythroid (BFU-E), or granulocyte-erythroid-macrophage-megakaryocyte (CFU-GEMM) cells, according to standard criteria (Humphreis et al. (1981) Proc. Natl. Acad. Sci. 76:3629–3633). The ability of a cell to form BFU-E units demonstrates that the cells are capable of developing into the erythroid lineage (Metcalf (1977) In: Recent Results in Cancer Research 61. Springer-Verlag, Berlin, pp. 1–227). In two experiments, identification of colony types was confirmed by Wright staining of cytospin preparations of colonies. For pre-B clonogenic progenitor assays, cells were plated in 0.8% methylcellulose in alpha medium supplemented with 30% FCS, $10^{-4}$M β-ME and 0.2 ng/ml of IL-7. Pre-B colonies were scored on day 7 of incubation.

Results. In three independent experiments, the gene transfer efficiency to clonogenic progenitors was similar for HOXB4 and control neo viruses, with 58%–70% of colonies showing G418 resistance. neo- or HOXB4-transduced bone marrow cells did not give rise to colonies in the absence of exogenous growth factors, showing that HOXB4 overexpression did not render clonogenic cells growth factor independent. Neither were there any differences detected in the proportion of different colony types generated by HOXB4- or neo-infected cells (assessed by both in situ scoring and by Wright staining of cytospin preparations of individually plucked colonies). This shows that HOXB4 overexpression also does not alter the ability of committed clonogenic progenitors to complete their differentiation into different types of mature blood cells. However, HOXB4-infected cells did give rise to significantly more large (i.e., >1000 cells/colony) granulocyte-macrophage colonies than what was observed in control cultures containing neo-transduced cells (41±14% vs. 16±14%, respectively) (n=3; $P<0.05$ two-tailed Student t-test). The majority of these large colonies had a diffuse morphology. Only rarely were dense colonies with a diffuse halo described by Perkins & Cory (1993) supra for bone marrow cells overexpressing HoxB8 seen in these experiments.

To further characterize the proliferative capacity of the HOXB4-infected cells, whole methylcellulose cultures were harvested 7 days after plating and various proportions assayed in secondary methylcellulose cultures. Cells harvested from the primary assays of HOXB4-infected cells were able to generate two- to three-fold more secondary colonies than neo-transduced control cells obtained from primary assays initiated with the same number of original input cells. One-third (32±0.8%) of the colonies obtained in the secondary cultures of HOXB4-transduced cells were large in size (>1000 cells/colony), whereas the proportion of such colonies in the assays of the replated neo-transduced cells was much lower (3.5±0.5%). To assess whether this increase in proliferation reflected a generalized effect of HOXB4 on the majority of clonogenic progenitors, well-isolated HOXB4- and neo-transduced G418-resistant colonies were picked at random either 7 days (FIG. 4) or 11 days (FIG. 5) after initiation of the primary cultures and one-third of each colony was then individually replated into secondary cultures. Under these conditions, <40% of neo-transduced colonies replated, yielding a mean of 80 and 180 secondary colonies per clone, whereas 80% of the individually analyzed HOXB4-transduced colonies replated, generating a mean of 320 and 1000 secondary colonies per clone, respectively (n=2; $P<0.005$, Student t-test).

Example 3

Colony Forming Unit (CFU-S) and Marrow Repopulating Ability (MRA) Assays

CFU-S Assay. Day-4 5-FU bone marrow cells were harvested after infection by co-cultivation with viral producers and injected immediately into lethally irradiated (B6C3)F$_1$ mice or after 1 week culture at an initial density of $1 \times 10^5$ to $5 \times 10^5$ cells/ml in 30% FCS, 1% BSA, $10^{-4}$M β-ME, 3 U/ml of Epo, 2% SCCM with or without 1.4 mg/ml of G418. The number of cells that each mouse received was adjusted to give 10–15 macroscopic spleen colonies ($2 \times 10^3$ to $4 \times 10^3$ bone marrow cells harvested from co-cultivation with virus producer cells or a proportion of the 1-week-old liquid cultures, described above, corresponding to $2 \times 10^3$ or $1 \times 10^5$ HOXB4- or neo-transduced input cells, respectively). CFU-S content of bone marrow cells obtained from mice transplanted 20 weeks earlier with neo- or HOXB4-infected cells was also evaluated by intravenous injection of $2 \times 10^5$ or $2 \times 10^4$ bone marrow cells/mouse, respectively. Untransplanted lethally irradiated mice were tested in each experiment for endogenous CFU-S surviving irradiation and consistently gave no spleen colonies. Twelve days after injection, animals were sacrificed by neck dislocation, and the number of macroscopic colonies on the spleen were evaluated after fixation in Telleyesniczky's solution.

MRA Assay. Lethally irradiated (B6C3)F$_1$ mice were injected intravenously with $2 \times 10^5$ day-4 5-FU bone marrow cells directly after they were harvested from the co-cultivation with viral producer cells or with a proportion of these cells kept for 7 days in the liquid culture described above, corresponding to $1.5 \times 10^5$ neo- or HOXB4-infected input cells. Thirteen days later, three mice per group were sacrificed and femoral cells were harvested, counted, and pooled. Dilutions corresponding to various proportions of a femur were then injected intravenously into lethally irradiated recipients for macroscopic spleen colony evaluation as described above. As a control to determine endogenous MRA surviving irradiation in primary recipients, half a femur, pooled from two untransplanted lethally irradiated mice, was assayed in three secondary recipients.

Figure 6:
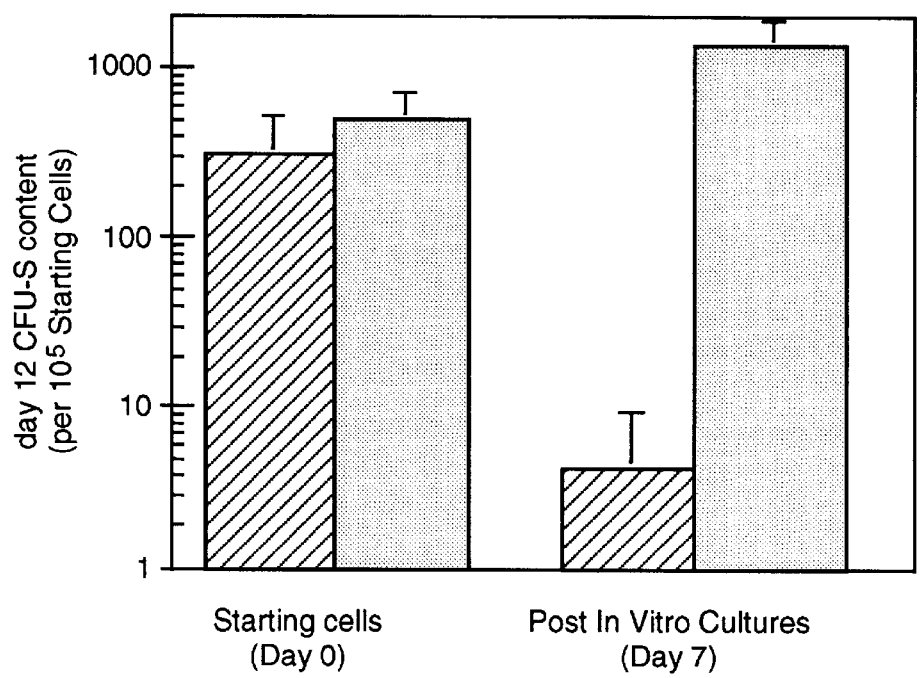
FIG. 6 is a bar diagram showing the effect of HOXB4 on day-12 colony forming units (CFU-S) in vitro. The CFU-S content of recovered cells was assessed immediately after co-cultivation (day 0) and after 7 days in liquid culture (day 7) in cultures initiated with HOXB4- (solid bar) or neo-transduced cells (hatched bar). Data is expressed as day-12 CFU-S colony numbers per $10^5$ starting day-0 cells. Results are the mean±S.D. from 4 independent experiments.

Results. Day-12 CFU-S frequencies of cells harvested immediately after co-cultivation with HOXB4 viral producers were similar to those obtained for the neo control (FIG. 6). However, after maintenance in liquid culture for 7 days (day 7) (FIG. 6), the CFU-S content of cultures initiated with neo-transduced cells was <1% of input, while the CFU-S content of cultures initiated with HOXB4-transduced cells increased to 200%–500% of input. As a result, there were ~200-fold more day-12 CFU-S in cultures initiated with the HOXB4-transduced bone marrow cells as compared with neo-transduced controls at the end of a 7-day period of incubation. Southern blot analysis of DNA extracted from 23 well-isolated spleen colonies produced in recipients of HOXB4-transduced cells showed each of the 23 colonies to be uniquely retrovirally marked, indicating that the two- to five-fold net expansion of day-12 CFU-S observed in these cultures was the result of a polyclonal expansion of HOXB4-transduced day-12 CFU-S or even an earlier cell type. Wright staining of cell preparations obtained from these spleen colonies showed a similar spectrum of late erythroid and myeloid elements compared with the neo control colonies (data not shown), indicating that HOXB4 overexpression does not affect the pattern of differentiation that day-12 CFU-S undergo during spleen colony formation in vivo.

MRA measured immediately after infection of bone marrow cells with the HOXB4 virus (day 0 after co-cultivation) was 10-fold higher than that measured for the neo-infected cells (FIG. 7). Following 7 days of liquid culture, the MRA content of the neo-transduced cells was undetectable (i.e., less than the background level of two day-12 CFU-S per femur), suggesting that the maintenance of MRA was compromised under the culture conditions used. In contrast, the MRA of the cells present in the day-7 cultures of HOXB4-transduced cells was maintained at readily detectable levels, and although reduced to 25% of input (day 0), this level was still >200-fold higher than that present at day-7 in control cultures of neo-transduced cells (FIG. 7).

Example 4

HOXB4-Induced Expansion In Vivo of Clonogenic Progenitors and Day-12 CFU-S

Competitive Repopulating Unit (CRU) Assay. Bone marrow cells pooled from three to four mice transplanted 12, 16, or 20 weeks earlier with neo- or HOXB4-transduced cells derived from (PepC3)$F_1$ (Ly5.1/Ly5/2) mice were injected at different dilutions into lethally irradiated (B6C3)$F_1$ (Ly5.2) mice together with a life-sparing dose of $1 \times 10^5$ competitor bone marrow cells from (B6C3)$F_1$ (Ly5.1) mice. The level of lymphomycloid repopulation with Ly5.1 donor-derived cells in these secondary recipients was evaluated >13 weeks later by flow cytometric analysis of peripheral blood as described (Rebel et al. (1994) supra) in all experiments but for the secondary recipient where it was evaluated at 5 weeks post-reconstitution. Recipients with >1% donor (Ly5.1)-derived peripheral blood lymphoid and myeloid leukocytes as determined by the side scatter distribution of Ly5.1$^+$ cells were considered to be repopulated by at least on CRU. CRU frequency in the test cell population was calculated by applying Poisson statistics to the proportion of negative recipients at different dilutions as described previously (Szilvassy et al. (1990) Proc. Natl. Acad. Sci. 87:8736–8740).

Results. Each mouse received an innoculum of $2 \times 10^5$ marrow cells estimated to contain ~30–40 CRUs, as subsequently determined (see Table 3). Gene transfer efficiencies in the transplant marrow as assessed by the proportion of G418-resistant in vitro clonogenic progenitors were 58±8% and 70±7% for HOXB4- and neo-transduced cells, respectively. This suggests that less than half of the CRUs in the transplant were transduced because frequencies of retroviral infection into these cells are typically lower than into in vitro clonogenic progenitors (Fraser et al. (1993) J. Immunol. 151:2409–2418). The extent of donor-derived reconstitution of peripheral blood leukocytes measured 12 or 20 weeks after transplantation was similar (>86%) for animals transplanted with either HOXB4-or neo-transduced marrow cells. Reconstitution of the hematopoietic system of recipients with both types of transduced cells was confirmed by Southern blot analysis of DNA extracted from bone marrow and spleen cells of mice sacrificed 20 weeks after transplantation. Northern blot analyses of RNA obtained from these tissues showed high levels of expression of HOXB4 and neo. Hematopoietic reconstitution by transduced cells was also confirmed by the high frequency of splenic and bone marrow G418-resistant myeloid clonogenic progenitors (75±17% and 42±18%, respectively, for recipients of HOXB4- and neo-infected cells).

The pre-B and myeloid clonogenic progenitor content of bone marrow 12 weeks after transplantation with HOXB4-transduced cells was on average two-fold higher than that of recipients of neo-infected cells (Table 1). Twenty weeks after transplantation with HOXB4-transduced marrow, an even greater increase in bone marrow and splenic clonogenic progenitor numbers was evident (5- and 32-fold higher, respectively, than in neo-transduced marrow recipients). To evaluate whether the increase in clonogenic progenitor cells numbers was accompanied by an expansion of an earlier cell type, day-12 CFU-S frequencies were also assessed in two independent experiments. In each of these, marrow cells from three mice transplanted 16 or 20 weeks earlier with either HOXB4- or neo-transduced cells were pooled and then assayed. By 16 to 20 weeks, the frequency of CFU-S in the recipients of control cells was back to normal (pretransplantation) levels (i.e., $1.0 \pm 0.3/10^4$ cells; Chang & Johnson (1991) supra), whereas in mice reconstituted with HOXB4-transduced bone marrow cells, the frequency of CFU-S was 5.0- and 7.6-fold higher, respectively, for the two time points.

Example 5

HOXB4-Induced Expansion In Vivo of Cells with Long-Term Lymphomycloid Repopulating Ability To determine if HOXB4 overexpression affects the expansion of the earliest hematopoietic cells, their numbers were quantified by limiting dilution analysis using the CRU assay (Szilvassy et al. (1990) Proc. Natl. Acad. Sci. 87:8736–8740, specifically incorporated by reference). Bone marrow cells, pooled from three mice transplanted either with HOXB4- or neo-transduced marrow cells 12 or 20 weeks earlier, were transplanted into lethally irradiated recipients following above-described procedures. The presence or absence of lymphomyeloid repopulation (>1%) with donor-derived Ly5.1$^+$ cells in these mice was then evaluated 13 or more weeks later, and CRU frequencies were calculated using Poisson statistics, from the proportion of recipients negative for donor-derived lymphomyeloid repopulation at different cell inocula (Szilvassy et al. (1990) supra).

By 12 weeks post-transplantation, recipients of neo-transduced marrow had reconstituted CRU to a frequency of 0.6 in $10^5$ bone marrow cells (Table 2) or only 6% that of normal (unmanipulated) mouse marrow (Szilvassy et al. (1990) supra). This low CRU frequency is consistent with the previously well-documented finding that even nonretrovirally infected marrow cells will not regenerate CRU numbers to >10% of pretransplant values (Harrison (1982) supra; Harrison et al. (1990) supra). For recipients of HOXB4-transduced marrow, a limiting dilution was not reached, suggesting that a CRU frequency of >2.9 in $10^5$ bone marrow cells, or at least 29% of normal levels, and >4-fold that seen in the recipients of neo-infected cells (Table 2).

CRU frequencies in the marrow was also measured in primary recipients sacrificed at 20 weeks after transplantation. The CRU frequency of the mice transplanted with neo-transduced marrow was similar to that obtained at 12 weeks, or ~3% of normal values (Table 2). In contrast, the frequency of CRU in recipients of HOXB4-infected marrow was 14 per $10^5$ cells. This represents a 1.4-fold increase above normal marrow values and a 47-fold increase above the CRU frequency measured in the marrow of recipients of control cells (Table 2).

Recipient mice used to quantitate CRUs (20 weeks post-transplant; Table 2) were further assessed by Southern blot analysis to identify those repopulated by transduced CRU. Southern blot analysis of proviral integration patterns in bone marrow and thymic DNA isolated from secondary recipients transplanted with varying numbers of HOXB4- or neo-transduced bone marrow was conducted. The number of bone marrow cells injected into each secondary recipient is as follows: neo: 667,000 cells (mice: 25.1, 25.2, 25.3); HOXB4: 33,000 cells (mice: 29.1, 29.2, 29.3, 30.1. 30.3), 11,000 cells (mice: 31.1, 31.2, 31.3, 31.4, 31.5, 32.1, 32.2), 6,700 cells (mice: 33.1, 33.2). DNA was digested with EcoRI that cuts the integrated MSCV provirus once generating DNA fragments specific to each integration site. The membranes were first hybridized to a probe for neo to identify proviral fragments, and subsequently to a probe for the erythropoietin receptor to provide a control for DNA loading. Exposure times were equivalent for both probes (~1 day). Primary mice used as donors were those sacrificed 20 weeks post-transplantation. The secondary recipients analyzed are as presented in Table 2. The percentage Ly5.1$^+$ cells in peripheral blood of the mice transplanted with HOXB4-transduced marrow was as follows: (animal (%)): 29.1 (30%), 29.2 (81%), 29.3 (39%), 30.1 (62%), 30.3 (30%), 31.1 (16%), 31.2 (3.2%), 31.3 (2%), 31.4 (29%), 31.5 (9%), 32.1 (1.1%), 32.2 (9%), 33.1 (44%), and 33.2 (6%).

Of 14 mice analyzed that received five or fewer CRUs from mice initially transplanted with HOXB4-infected marrow, 12 were positive for proviral integration in thymic and/or bone marrow tissue, all of which had been scored previously as positive for donor-derived Ly5.1 lymphomyeloid repopulation in the CRU assay. Moreover, common proviral integration patterns for thymic and bone marrow tissues were clearly apparent in five of these secondary recipients, confirming the lymphomyeloid repopulating potential of the regenerated CRU. The intensities of the proviral integration signals also roughly correlated with the percentages of donor-derived Ly5.1 cells in the peripheral blood. For two mice who were scored as negative for donor-derived lymphomyeloid repopulation, proviral integrants were not detected. This correlation indicates that HOXB4-transduced HSCs can terminally differentiate in vivo and in vitro. These results indicate that the measured CRU expansion in vivo was the result of the selective expansion of HOXB4-transduced CRUs. In contrast, four recipients of marrow from primary mice initially transplanted with neo-infected bone marrow were all negative for proviral integrants, but positive for donor Ly5.1 cells, indicating that CRU regeneration in the primary mice included nontransduced CRUs.

Self-renewal of HOXB4-transduced CRUs was also demonstrated by detection of the same pattern of proviral DNA integration in thymus and bone marrow cells of four different secondary recipients (mice 29.1, 30.3, 33.1, and 30.1). Another uniquely identified totipotent CRU was detected in recipient 29.2. Self-renewal of a CRU with apparent subsequent restriction to the marrow was detected in secondary recipients 31.2, 31.5, 32.2, and 33.2. These latter mice, however, showed lymphomyeloid repopulation by FACS analysis of Ly-5.1-positive peripheral blood leukocytes suggesting that this clone had B-lymphoid and myeloid potential. The degree of self-renewal detected is consistent with the marked expansion of CRUs observed in primary animals (nearly 900-fold; Table 3) and the fact that mice were initially transplanted with small numbers of CRUs (~32, of which at most half would be estimated to have been transduced).

To further assess the regenerative capacity of HOXB4-transduced CRUs, their expansion in secondary recipients was also evaluated. Bone marrow cells were harvested from secondary recipients (n=3 for neo and n=5 for HOXB4) transplanted 16 weeks earlier with about two to five Ly5.1$^+$ CRUs (Table 2) and CRU frequencies measured by limit dilution analysis in tertiary recipients. CRU frequency in the secondary recipients of neo-transduced marrow was 1 in $4.8 \times 10^6$ cells (Table 2), or <0.2% of that found in normal unmanipulated marrow, and indicative of a 17-fold expansion over input (summarized in Table 3). In sharp contrast, secondary recipients of HOXB4-transduced marrow had a CRU frequency of 130 times higher, or ~20% of normal levels, and were indicative of a further 900-fold expansion over input (Table 3).

Despite this dramatic expansion of HOXB4-transduced HSCS, it is noteworthy that the relative numbers of the various types of in vitro myeloid clonogenic progenitors (i.e.g, CFU-GM, BFU-E, and CFU-GEMM) in primary and secondary recipients of HOXB4-infected cells were the same as in recipients of control cells. In addition, the total cellularity of the bone marrow was also not different, and the red blood cells, white blood cell, and differential counts were also within the normal range (n=9 for each group in the 16- to 34-week observation period)(data not shown). Thus, despite a marked and sustained effect of HOXB4 overexpression on the numbers of myeloid and lymphoid clonogenic progenitors as well as day-12 CFU-S, there was no gross effect on lineage determination nor evidence of subsequent expansion of later cell types. Moreover, despite a significant expansion in the numbers of the most primitive hematopoietic cells, none of the primary recipients (n=25) of HOXB4-transduced marrow have developed leukemia or any other obvious blood dyscrasia for an observation period now extending to 12 months post-transplantation.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2018 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAATTCGGGT  TAGTATATTT  TGTGGGCAAT  TCCCAGAAAT  TAATGGCTAT  GAGTTCTTTT        60
```

-continued

| | | | | | | |
|---|---|---|---|---|---|---|
|TTGATCAACT|CAAACTATGT|CGACCCCAAG|TTCCCTCCAT|GCGAGGAATA|TTCACAGAGC|120|
|GATTACCTAC|CCAGCGACCA|CTCGCCCGGG|TACTACGCCG|GCGGCCAGAG|GCGAGAGAGC|180|
|AGCTTCCAGC|CGGAGGCGGG|CTTCGGGCGG|CGCGCGGCGT|GCACCGTGCA|GCGCTACGCG|240|
|GCCTGCCGGG|ACCCTGGGCC|CCCGCCGCCT|CCGCCACCAC|CCCCGCCGCC|CCCGCCACCG|300|
|CCCGGTCTGT|CCCCTCGGGC|TCCTGCGCCG|CCACCCGCCG|GGGCCCTCCT|CCCGGAGCCC|360|
|GGCCAGCGCT|GCGAGGCGGT|CAGCAGCAGC|CCCCGCCGC|CTCCCTGCGC|CCAGAACCCC|420|
|CTGCACCCCA|GCCCGTCCCA|CTCCGCGTGC|AAAGAGCCCG|TCGTCTACCC|CTGGATGCGC|480|
|AAAGTTCACG|TGAGCACGGT|AAACCCCAAT|TACGCCGGCG|GGGAGCCCAA|GCGCTCTCGG|540|
|ACCGCCTACA|CGCGCCAGCA|GGTCTTGGAG|CTGGAGAAGG|AATTTCACTA|CAACCGCTAC|600|
|CTGACACGGC|GCCGGAGGGT|GGAGATCGCC|CACGCGCTCT|GCCTCTCCGA|GCGCCAGATC|660|
|AAGATCTGGT|TCCAGAACCG|GCGCATGAAG|TGGAAAAAAG|ACCACAAGTT|GCCCAACACC|720|
|AAGATCCGCT|CGGGTGGTGC|GGCAGGCTCA|GCCGGAGGGC|CCCTGGCCG|GCCCAATGGA|780|
|GGCCCCCGCG|CGCTCTAGTG|CCCCCGCACG|CGGGAGCCAC|GAACCTCGGG|GTGGGGGTGG|840|
|GCAGTGAGTG|CAGGGGATGG|GGTGGGGGA|CAGGAGGGGG|CCCTGCCTGG|GCCCCGGAAA|900|
|AATCTATCTG|CCCTCCCCCA|CACTTTATAT|ACGAATAAAC|GCAGAAGAGG|GGGAGGGGAA|960|
|GCTTTATTTA|TATAAATGAC|AATAGAGGGC|CACGGGGAGG|CCCCCCAGA|AGCAAGATTC|1020|
|AAATCTCTTG|CTTTCTTTCT|TAAAAAAAAG|AAAAGAAAA|AGCAAGAAGA|AGGAAGAAAG|1080|
|AAAAAGACAG|AAAGAGATAT|AGGAGGAGGC|TGCAGCTCCT|CGTTTTCAGC|TTTGGCGAAG|1140|
|ATGGATCCAC|GTTTCATCTT|TAATCACGCA|GGTCCAGGCC|CATCTGTTTT|GTTTCCTCTG|1200|
|CCGAGGAGAA|GACGGGCCTC|GGTCGCGACC|ATTACCTCGA|CACCCGCTAA|CAAATGAGGC|1260|
|CCGGCTCGGC|GTCTCCGCCT|CTGCTACTGC|CGCTGCTGGA|AGACAGCCTG|GATTTCCTTT|1320|
|CTTTGTCCCC|CACTCCCGAT|ACCCAGCGAA|AGACCCTCTG|ACTGCCAGAT|AGTGCAGTGT|1380|
|TTTGGTCACG|GTAACACACA|CACACTCTCC|CTCATCTCTC|GTGCCCATTC|ACTGAGGGCC|1440|
|AGAATGACTG|CACACCCACT|TCCACCGTGG|GGTTGGGGGT|GGGCAACAGA|GGAGGGAGC|1500|
|AAGTAGGGAA|GGGGGTGGCC|TTGACAACTC|AGGAGTGAGC|AGGGAAATTG|AGTCCAAGGA|1560|
|AAAAGAGAGA|CTCAGAGACC|CGGGAGGCCT|TCCTCTGAAG|GCCAAGCCAA|GCCATGCTTG|1620|
|GCAGGGTGAG|GGGCCAGTTG|AGTTCTGGGA|GCTGGGCACT|ACTCTGCCAG|TCCAGAGTTG|1680|
|TACAGCAGAA|GCCTCTCTCC|TAGACTGAAA|ATGAATGTGA|AACTAGGAAA|TAAAATGTGC|1740|
|CCCTCCCAGT|CTGGGAGGAG|GATGTTGAAG|AGCCCTCTCC|CATAGTTTAT|TATGTTGCAT|1800|
|CGTTTATTAT|TATTATTGAT|AATATTATTA|TTACTATTTT|GTTGTGTCAT|GTGAGTCCTC|1860|
|TCTCCTTTTC|TCTTTCTGAC|ATTCCAAAAC|CAGGCCCTT|CCTACCTCTG|GGGCTGCTTG|1920|
|AGTCTAGAGC|CCTTCGTATG|TGTGAATATC|TGTGTGCTGT|ACAGAGTGAC|AATAGAAATA|1980|
|AATGTTTGGT|TTCTTGTGAA|AAAAAAAAC|CCGAATTC| | |2018|

What is claimed is:

1. A stem cell modified to express an exogenous gene, wherein said gene is a HOX gene selected from the group consisting of a class HOXA, HOXB, HOXC, and HOXD gene, and wherein said modified stem cell has an enhanced ability to proliferate to form an expanded population of pluripotent stem cells.

2. The modified stem cell of claim 1, wherein said modified stem cell has a 10- to 100-fold enhanced ability to proliferate while maintaining pluripotent characteristics of its unmodified parent.

3. The modified stem cell of claim 1, wherein said modified stem cell has a 50- to 100-fold enhanced ability to proliferate while maintaining pluripotent characteristics of its unmodified parent.

4. The modified stem cell of claim 1, wherein said modified cell is a hematopoietic cell.

5. The modified stem cell of claim 1, wherein said modified cell is a mammalian cell.

6. The modified stem cell of claim 5, wherein said mammalian cell is a human stem cell.

7. The modified stem cell of claim 6, wherein said HOX gene is a human HOX gene.

8. The modified stem cell of claim 6, wherein said cell is CD34$^+$.

9. The stem cell of claim 8, wherein said HOX gene is HOXB.

10. The stem cell of claim 9, wherein said HOXB gene is HOXB4.

11. The stem cell of claim 1, wherein said cell is modified by transfection with a retroviral vector containing the HOXB4 gene.

12. An expanded stem cell population, wherein said cells are modified to express an exogenous HOX gene, and wherein said HOX gene is a Hox gene selected from the group consisting of a class HOXA, HOXB, HOXC, and HOXD gene, and said population has the ability to undergo substantial self-renewal while maintaining pluripotent characteristics.

13. The expanded stem cell population of claim 12, wherein said stem cell is a hematopoietic cell.

14. The expanded stem cell population of claim 13, wherein pluripotent means having the ability to give rise to all hematopoietic cell lineages.

15. A method for expanding a population of stem cells, comprising modifying a stem cell to express an exogenous HOX gene wherein said HOX gene is selected from a group consisting of a class HOXA, HOXB, HOXC, and HOXD gene.

16. The method of claim 15, wherein said modified stem cell is a hematopoietic cell characterized by the ability to undergo substantial self-renewal and ability to give rise to all hematopoietic cell lineages.

17. A therapeutic method for restoring hematopoietic capability to a mammalian subject, said method comprising the steps of:

(a) removing hematopoietic stem cells from a mammalian subject;

(b) modifying said stem cells to express a HOX gene selected from the group consisting of a class HOXA, HOXB, HOXC, and HOXD gene;

(c) expanding said stem cells to form an expanded population of stem cells from said subject, and (d) returning said expanded cells to said subject, wherein hematopoietic capability is restored to said subject.

18. The method of claim 17, wherein said expanded cells are characterized by the ability to undergo substantial self-renewal and ability to give rise to all hematopoietic cell lineages.

* * * * *